United States Patent [19]

Champseix et al.

[11] 4,405,789
[45] Sep. 20, 1983

[54] 2 PHENYL-3-CHLORO-4[PIPERIDYL ALKYL]QUINOLINES

[75] Inventors: Alain A. Champseix, Orsay; Gerard R. Le Fur, Plessis Robinson, both of France

[73] Assignee: Pharmindustrie, Gennevilliers, France

[21] Appl. No.: 237,784

[22] Filed: Feb. 24, 1981

[30] Foreign Application Priority Data

Mar. 7, 1980 [FR] France .................. 80 05152

[51] Int. Cl.³ .................. C07D 401/06; A61K 31/47
[52] U.S. Cl. .................. 546/176; 424/258
[58] Field of Search .................. 546/176, 180

[56] References Cited
FOREIGN PATENT DOCUMENTS 7618555 1/1978 France .

Primary Examiner—Nicholas S. Rizzo
Assistant Examiner—D. B. Springer
Attorney, Agent, or Firm—Beveridge, DeGrandi & Kline

[57] ABSTRACT

Compounds useful as medicaments, of the formula:

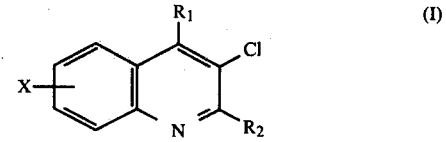

in which X is hydrogen, halogen, alkyl containing 1 to 4 carbon atoms, alkoxy containing 1 to 4 carbon atoms or alkylthio containing 1 to 4 carbon atoms, one of the substituents $R_1$ and $R_2$ is hydrogen, alkyl containing 1 to 4 carbon atoms, phenyl or phenyl substituted by halogen, alkyl containing 1 to 4 carbon atoms, alkoxy containing 1 to 4 carbon atoms, alkylthio containing 1 to 4 carbon atoms, trifluoromethyl, nitro, unsubstituted amino or amino substituted by one or two alkyl containing 1 to 2 carbon atoms, and the other of the substituents $R_1$ and $R_2$ is a group of the formula:

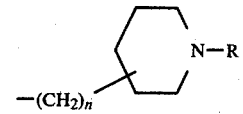

in which n is 1, 2 or 3 and R is hydrogen or alkyl containing 1 to 4 carbon atoms.

4 Claims, No Drawings

2 PHENYL-3-CHLORO-4[PIPERIDYL ALKYL]QUINOLINES

The present invention relates to new derivatives of 3-chloro-quinoline which may be used as medicaments.

These derivatives may be represented by the general formula:

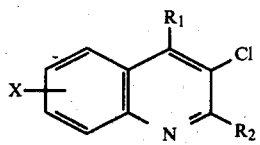

in which X is fixed in position 5, 6, 7 or 8 on the quinoline ring and represents a hydrogen or halogen (chlorine, fluorine, bromine, iodine) atom or an alkyl, alkoxy or alkylthio group, each having 1 to 4 carbon atoms, one of the substituents $R_1$ and $R_2$ is a hydrogen atom, an alkyl group having 1 to 4 carbon atoms, an unsubstituted phenyl group or a phenyl group substituted by one or two substituents selected from the halogen atoms (chlorine, fluorine, bromine, iodine), the alkyl, alkoxy or alkylthio groups each having 1 to 4 carbon atoms, the trifluoromethyl, nitro or unsubstituted amino groups, and the amino group substituted by one or two alkyl groups having 1 or 2 carbon atoms, and the other of the substituents $R_1$ and $R_2$ is a piperidylalkyl group of the formula:

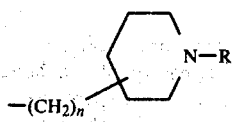

in which n is a whole number 1, 2 or 3, R is a hydrogen atom or an alkyl group having 1 to 4 carbon atoms, and the radical $(CH_2)_n$ is fixed in position 2, 3 or 4 on the piperidine ring.

In the foregoing formula (I) X is preferably a hydrogen atom, $R_2$ is preferably a hydrogen atom or a methyl or phenyl group, and $R_1$ is preferably a group of the formula:

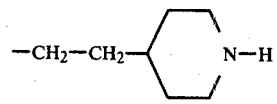

The compounds of general formula (I) for which R is a hydrogen atom may be prepared by the action of dichlorocarbene: $CCl_2$ on indole derivatives of formula (II) or (IIa) and hydrolysis of the N-formyl derivatives of formula (III) or (IIIa) thus obtained, according to the following reaction scheme:

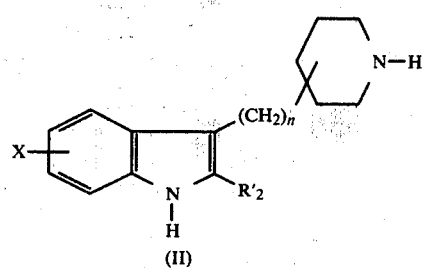 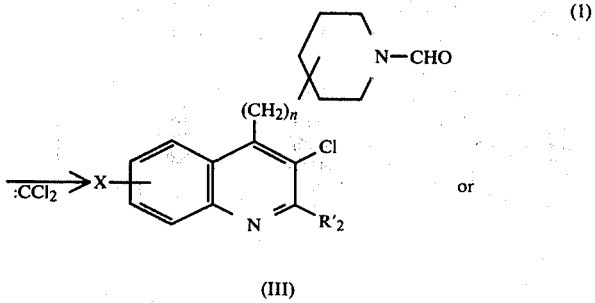

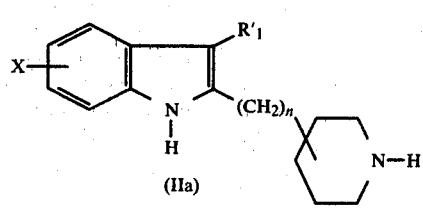 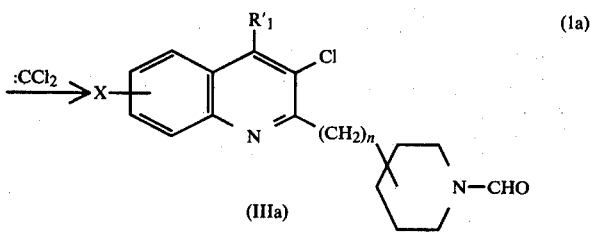

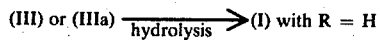

In the formulae (II), (IIa), (III) and (IIIa), X and n have the same significance as in formula (I), and $R'_2$ and $R'_1$ represent a hydrogen atom, an alkyl group having 1 to 4 carbon atoms, an unsubstituted phenyl group or a phenyl group substituted by one or two substituents selected from the halogen atoms, the alkyl, alkoxy or alkylthio groups each having 1 to 4 carbon atoms, $CF_3$, $NO_2$, $NH_2$ and the amino group substituted by one or two alkyl groups having 1 to 2 carbon atoms.

The indole derivatives of formulaw (II) and (IIa) are known compounds or compounds which may be prepared by known processes (cf. for example: DeGraw et al., J. Heterocyclic Chem. 3(1), 67–69, 1966; Tacconi et al., Farmaco (Pavia), Ed. Sci. 20(7), 470–481; 1965; Gray et al., Journal of Organic Chemistry, 26, 3368–3372, 1961; British Pat. No. 1,023,781; French Patent of Medicine 1693 M based on the priority of U.S. application Ser. No. 19,157 filed Apr. 1, 1960 in the name of Allen Poe Gray; French Pat. No. 2,334,358 which is the equivalent of British Pat. No. 1,561,111 and U.S. Pat. No. 4,064,225).

The dichlorocarbene used in reactions (1) and (1a) is prepared "in situ" by the action of a base on chloroform. The reactions (1) and (1a) may be effected advantageously by stirring a solution of a suspension of the indole derivative of formula (II) or (IIa) in the chloroform with an aqueous solution of sodium hydroxide (in particular a 50% aqueous solution of sodium hydroxide), in the presence of a quaternary ammonium salt such as for example, benzyltriethylammonium chloride.

The hydrolysis reaction (2) may be effected by heating, preferably at the boil, the intermediate compound of formula (III) or (IIIa) in an aqueous solution of an acid such as hydrochloric or sulfuric acid.

The compounds of general formula (I) for which R is an alkyl group may be prepared by the action of an alkylating agent, such as an alkyl halide of the formula RCl or RBr, on the corresponding compounds of formula (I) for which R is a hydrogne atom. The alkylation reaction is effected according to processes known per se (cg. R. B. Wagner and H. D. Zook, Synthetic Organic Chemistry, p. 666, J. Wiley and Sons, 1965). Advantageously the operation is effected in the presence of an organic or mineral base (for example sodium or potassium carbonate) in an inert solvent such as dimethylformamide.

The compounds of general formula (I) for which R is an alkyl group are preferably prepared by a process in two stages which consists in reacting in a first stage the corresponding compounds of formula (I) for which R is a hydrogen atom with a compound of the formula

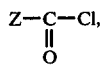

in which Z represents an alkyl group having 1 to 3 carbon atoms or a lower alkoxy group (for example methoxy or ethoxy), and then reducing the compounds of formula (IV) or (IVa) thus obtained with a hydride. The reaction scheme is as follows:

Organic Chemistry, p. 565 and p. 646, J. Wiley and Sons, 1953). The operation is generally effected in the presence of a base such as sodium hydroxide in aqueous solution or triethylamine, in an inert solvent such as chloroform or 1,1,1-trichloroethane, at a temperature between 0° C. and 30° C.

Reaction (4) also uses known methods (cf. for example R. B. Wagner and H. D. Zook, Synthetic Organic Chemistry, p. 660, J. Wiley and Sons, 1953). As the reducing hydride there is advantageously used lithium aluminum hydride or other complex hydrides such as the hydride of sodium and bis(2-methoxy-ethoxy) aluminum, in an inert solvent such as an ether or an aromatic hydrocarbon. In reaction (4) the —CO—Z group is converted into the group —CH$_2$—Z in the case where Z is an alkyl group, and into the methyl group in the case where Z is a lower alkoxy group.

The reaction mixtures obtained by the various processes previously described are treated according to conventional methods, physical methods (evaporation, extraction by means of a solvent, distillation, crystallization, chromatography, etc.) or chemical methods (formation of the salt and regeneration of the base, etc.), in order to isolate the compounds of formula (I) in the pure state.

The compounds of formula (I) in the form of the free base may if desired be converted into salts of addition with a mineral or organic acid by the action of such an acid in a suitable solvent.

The medicaments of the benzodiazepines class are used as anti-convulsants, as hypnotics and for the treatment of states of anxiety and of various psychoneurotic states. The presence of specific receptors of the benzodiazepines in the membranes of the brain of the rat has been demonstrated [Squires et al., Nature, 266, (1977), 732] and the degree of affinity of the benzodiaze-

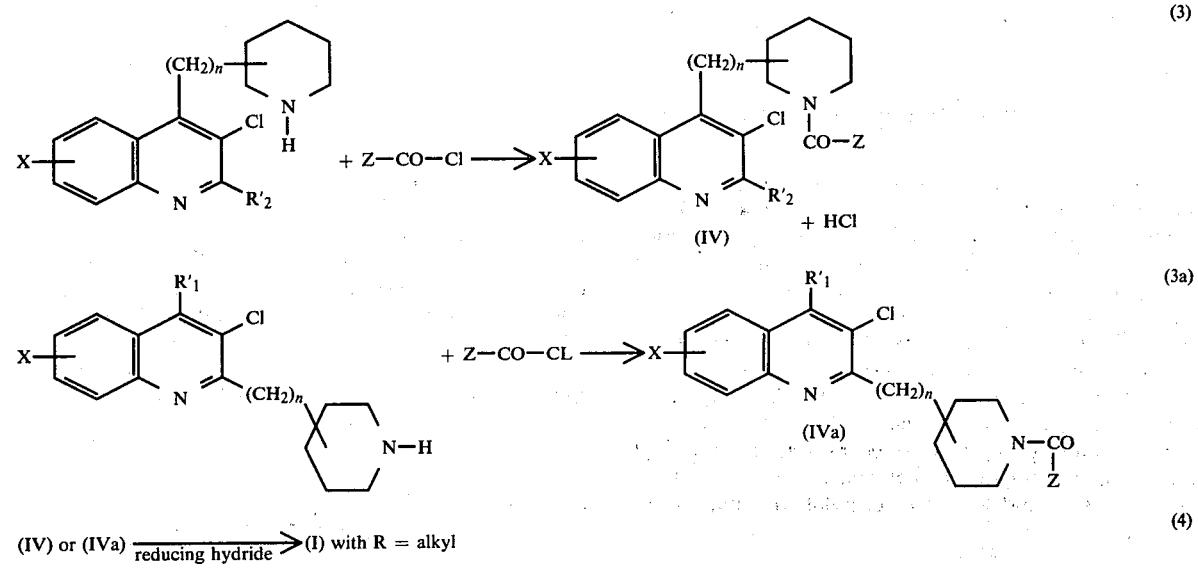

In the formulae intervening in the above reaction scheme, R'$_1$ and R'$_2$ have the significance previously indicated, and X and n have the same significance as in formula (I).

To carry out reactions (3) and (3a), methods known per se are used which enable a secondary amine to be converted into an amide (when Z=alkyl) or into a carbamate (when Z=alkoxy), for example those described by R. B. Wagner and H. D. Zook (Synthetic pines for these receptors, which degree of affinity is measured by the capacity of the benzodiazepines for displacing the tritiated Diazepam from its binding sites, is in good correlation with the pharmacodynamic effects observed with animals and with man.

Up to now, apart from the benzodiazepines, no medicament acting on the central nervous system has shown itself capable of significantly displacing Diazepam from its binding sites [cf. Braestrup et al., Europ. J. Pharmacol., 48, (1978) 26].

The products of the invention, although structurally different from the benzodiazepines, displace Diazepam from its binding sites. They can then find applications as hypnotics, anticonvulsants, and in the treatment of states of tension and anxiety resulting from circumstances causing stress or somatic disturbances related to emotional factors. They can be used for the treatment of the psychoneurotic states which are manifested by symptoms of anxiety, apprehension, fatigue, agitation or depression.

The following specific examples illustrate the invention without limiting it. The data relative to the nuclear magnetic resonance spectra (in short: N.M.R. spectra) given in these examples relate to the nuclear magnetic resonance of the protons of the compounds in the form of the free base. In order to carry out the N.M.R. measurements the compounds are dissolved in deuteriated chloroform. The reference used is tetramethylsilane.

EXAMPLE 1

3-Chloro-4-[2-(4-piperidyl)-ethyl]-quinoline

A solution of 60 g of sodium hydroxide in 120 ml of water is slowly added over a period of two hours, while maintaining at the ambient temperature (about 20° C.), to a well stirred suspension of 45.8 g of 4-[2-(3-indolyl)-ethyl]-piperidine and 1 g of benzyltriethylammonium chloride in 500 ml of chloroform free from ethanol. The dissolution is progressive. After 72 hours at ambient temperature, the two phases are separated by decantation. The aqueous phase is extracted twice with 100 ml of chloroform. The organic phases are collected and concentrated by removal of the chloroform.

The residue obtained is heated under reflux for one hour in 400 ml of 5 N aqueous solution of hydrochloric acid. After cooling to 0° C., the mixture is made alkaline by means of 250 ml of a 10 N aqueous solution of sodium hydroxide, then extracted with 300 ml of chloroform. The organic phase is washed with 500 ml of water, dried over magnesium sulfate, then concentrated by elimination of the chloroform. 61.2 g of an oily product are thus obtained. This product is fixed on a silica column, then eluted by a 90/10 chloroform-diethylamine mixture. 35 g of 3-chloro-4-[2-(4-piperidyl)-ethyl]-quinoline are obtained, the hydrochloride of which melts at 190° C.

N.M.R. spectrum of the product obtained:
The chemical displacements δ of the protons are as follows:

| aromatics | δ: 7.3–8.8 ppm |
| CH$_2$—N and CH$_2$—Ar | δ: 2.3–3.4 ppm |

EXAMPLE 2

3,5-Dichloro-4-[2-(4-piperidyl)-ethyl]-quinoline

The operation is as in Example 1, but starting from 11 g of 4-[2-(5-chloro-3-indolyl)-ethyl]-piperidine and 0.21 g of benzyltriethylammonium chloride in suspension in 100 ml of chloroform and 12.5 g of sodium hydroxide in solution in 25 ml of water. 2 g of 3,6-dichloro-4-[2-(4-piperidyl)-ethyl]-quinoline are finally obtained in the form of the dihydrochloride melting at 248° C.

N.M.R. spectrum of the product obtained:

| aromatics | δ: 7.3–8.7 ppm |
| CH$_2$Ar and CH$_2$N | δ: 2.5–3.4 ppm |

EXAMPLE 3

3-Chloro-6-methoxy-4-[2-(4-piperidyl)-ethyl]-quinoline

The operation is as in Example 1, but starting from 15 g of 4-[2-(5-methoxy-3-indolyl)-ethyl]-piperidine and 0.25 g of triethylbenzylammonium chloride in 120 ml of chloroform and 18 g of sodium hydroxide in 35 ml of water. 1.85 g of 3-chloro-6-methoxy-4-[2-(4-piperidyl-ethyl]-quinoline are finally obtained in the form of the dihydrochloride melting at 210° C.

N.M.R. spectrum of the product obtained:

| aromatics | δ: 7.1–8.7 ppm |
| CH$_2$N and CH$_2$Ar | δ: 2.2–3.4 ppm |
| CH$_3$O | δ: 4 ppm |

EXAMPLE 4

2-Methyl-3-chloro-4-[2-(4-piperidyl)-ethyl]-quinoline

The operation is as in Example 1, but starting from 5.9 g of 4-[2-(2-methyl-3-indolyl)-ethyl]-piperidine and 0.12 g of triethylbenzylammonium chloride in 60 ml of chloroform and 7.5 g of sodium hydroxide in 15 ml of water. 2.7 g of 2-methyl-3-chloro-4-[2-(4-piperidyl)-ethyl]-quinoline are finally obtained in the form of the monohydrochloride which melts at 255° C.

N.M.R. spectrum of the product obtained:

| aromatics | δ: 7.4–8.2 ppm |
| CH$_3$Ar | δ: 2.8 ppm |
| CH$_2$N and CH$_2$Ar | δ: 2.4–3.4 ppm |

EXAMPLE 5

2-Phenyl-3-chloro-4-[2-(4-piperidyl)-ethyl]-quinoline

The operation is as in Example 1, but starting from 12 g of 4-[2-(2-phenyl-3-indolyl)-ethyl]-piperidine and 0.2 g of triethylbenzylammonium chloride in 110 ml of chloroform and 12 g of sodium hydroxide in 24 ml of water. 1.05 g of 2-phenyl-3-chloro-4-[2-(4-piperidyl)-ethyl]-quinoline are finally obtained in the form of the hydrochloride melting at 233° C.

N.M.R. spectrum of the product obtained:

| aromatics | δ: 7.2–8.4 ppm |
| CH$_2$N and CH$_2$Ar | δ: 2.2–3.4 ppm |

The starting substance, 4-[2-(2-phenyl-3-indolyl)-ethyl]-piperidine, was prepared in the following way:

A well stirred suspension containing 39.5 g of 4-[2-(2-phenyl-3-indolyl)-ethyl]-pyridine in solution in 40 ml of acetic acid and 2 g of Adams platinum oxide is maintained at the ambient temperature under a pressure of hydrogen corresponding to an excess pressure of 50 mm of water with respect to the atmospheric pressure, until absorption of gas ceases.

The platinum is then separated by filtration and the acetic acid solution is concentrated by evaporation. The oily residue obtained is made alkaline by addition of an 11 N aqueous solution of sodium hydroxide and is extracted by 500 ml of chloroform. The chloroform phase is dried over magnesium sulfate, then concentrated by elimination of the chloroform. 37.8 g of 4-[2-(2-phenyl-3-indolyl)-ethyl]-piperidine are thus obtained which melts at 183° C.

N.M.R. spectrum of the product obtained:

| aromatics | δ: 7.2–7.8 ppm |
| --- | --- |
| $CH_2Ar$ and $CH_2N$ | δ: 2.4–3.3 ppm |

The 4-[2-(2-phenyl-3-indolyl)-ethyl]-pyridine was prepared by the method of P. Bruni, Ann. Chim. (ROME) 1957, 57 (4), 376-81.

EXAMPLE 6

3-Chloro-4-[(4-piperidyl)-methyl]-quinoline

The operation is as in Example 1, but starting from 13.4 g of 4-(3-indolyl-methyl)-piperidine and 0.54 g of triethylbenzylammonium chloride in 130 ml of chloroform and 19.5 g of sodium hydroxide in solution in 39 ml of water. 4.2 g of 3-chloro-4-[(4-piperidyl)-methyl]-quinoline are finally obtained in the form of the dihydrochloride melting above 260° C.

N.M.R. spectrum of the product obtained.

| aromatics | δ: 7.3–9 ppm |
| --- | --- |
| $CH_2Ar$ | δ: 3.2 ppm |

EXAMPLE 7

3-Chloro-6-methoxy-4-[(4-piperidyl)-methyl]-quinoline

The operation is as in Example 1, but starting from 10.2 g of 4-[(5-methoxy-3-indolyl)-methyl]-piperidine and 0.21 g of triethylbenzylammonium chloride in 100 ml of chloroform, and 12.5 g of sodium hydroxide in solution in 25 ml of water. 3.7 g of 3-chloro-6-methoxy-4-[(4-piperidyl)-methyl]-quinoline are finally obtained, the monohydrochloride of which melts above 260° C.

N.M.R. spectrum of the product obtained:

| aromatics | δ: 7.2–9 ppm |
| --- | --- |
| $CH_3O$ | δ: 4 ppm |
| $CH_2Ar$ | δ: 3.2 ppm |

EXAMPLE 8

3-Chloro-8-methyl-4-[(4-piperidyl)-methyl]-quinoline

The operation is as in Example 1, but starting from 9.5 g of 4-[(7-methyl-3-indolyl)-methyl]-piperidine and 0.21 g of triethylbenzylammonium chloride in 100 ml of chloroform, and 12.5 g of sodium hydroxide in solution in 25 ml of water. 5.1 g of 3-chloro-8-methyl-4-[(4-piperidyl)-methyl]-quinoline are finally obtained, the monohydrochloride of which melts at 252° C.

N.M.R. spectrum of the product obtained:

| aromatics | δ: 7.3–8.8 ppm |
| --- | --- |
| $CH_3-Ar$ | δ: 2.8 ppm |
| $CH_2-Ar$ | δ: 3.2 ppm |

EXAMPLE 9

3-Chloro-2-[2-(4-piperidyl)-ethyl]-quinoline

The operation is as in Example 1, but starting from 8.3 g of 4-[2-(2-indolyl)-ethyl]-piperidine and 0.18 g of triethylbenzylammonium chloride in 90 ml of chloroform, and 11 g of sodium hydroxide in solution in 22 ml of water. 1.45 g of 3-chloro-2-[2-(4-piperidyl)-ethyl]-quinoline are obtained the monohydrochloride of which melts at 162° C.

N.M.R. spectrum of the product obtained:

| aromatics | δ: 7.4–8.2 ppm |
| --- | --- |
| $CH_2Ar$ and $CH_2-N$ | δ: 2.5–3.6 ppm |

The starting product, 4-[2-(2-indolyl)-ethyl]-piperidine, may be prepared as follows:

300 g of phosphoric anhydride are progressively added, portionwise, to 150 ml of 85% orthophosphoric acid which is well stirred, the temperature being maintained below or equal to 100° C. by cooling with a water-bath. When the medium is quite homogeneous, 11.4 g of 4-[2-(3-indolyl)-ethyl]-piperidine are introducted, then the reaction medium is heated at 150° C. for 45 minutes. The syrupy liquid obtained is slowly introduced into 3 kg of an ice+water mixture, then the pH is brought to 10 by addition of 800 ml of an 11 N aqueous solution of sodium hydroxide. The product is extracted four times by 300 ml of ethyl acetate. The extracts are collected, washed with 100 ml of water, dried over magnesium sulfate and concentrated by elimination of the ethyl acetate. 8.2 g of 4-[2-(2-indolyl)-ethyl]-piperidine are thus obtained which melts at 191° C.

EXAMPLE 10

3-Chloro-4-[2-(3-piperidyl)-ethyl]-quinoline

The operation is as in Example 1, but starting from 3.8 g of 3-[2-(3-indolyl)-ethyl]-piperidine and 0.075 g of benzyltriethylammonium chloride in 40 ml of chloroform, and 5 g of sodium hydroxide in 10 ml of water. 1.3 g of 3-chloro-4-[2-(3-piperidyl)-ethyl]-quinoline are finally obtained in the form of the dihydrated monohydrochloride melting at 75° C.

The starting substance 3-[2-(3-indolyl)-ethyl]-piperidine may be prepared in the following way:

A solution of 9.7 g of 3-indolyl-(3-piperidyl-methyl)-ketone in 500 ml of anhydrous dioxan is added, drop by drop, under an atmosphere of nitrogen, to a suspension of 3 g of lithium aluminum hydride in 500 ml of anhydrous dioxan. The mixture is heated with reflux for 3 hours, then cooled to 0° C. and 15 ml of water and 24 ml of a 15% aqueous solution of sodium hydroxide are successively added. The insoluble mineral products formed are separated by filtration and the filtrate is dried over magnesium sulfate and evaporated. 4 g of 3-[2-(3-indolyl)-ethyl]-piperidine are thus obtained in the form of an oil.

The 3-indolyl-(3-piperidyl-methyl)-ketone can be prepared by the process described in French Pat. No. 2,334,358.

EXAMPLE 11

3-Chloro-6-methoxy-4-[2-(1-methyl-4-piperidyl)-ethyl]-quinoline 6 ml of a 1 N aqueous solution of sodium hydroxide, cooled to 0° C., is added with stirring to a solution of 1.8 g of 3-chloro-6-methoxy-4-[2-(4-piperidyl)-ethyl]-quinoline in 6 ml of chloroform. 0.49 g of ethyl chloroformate is then added drop by drop.

The suspension obtained is stirred for some hours, then decanted. The organic phase is washed with water, dried over magnesium sulfate, then concentrated. 1.6 g of 3-chloro-6-methoxy-4-[2-(1-ethoxycarbonyl-4-piperidyl)-ethyl]-quinoline in the form of an oil is thus obtained.

0.38 g of lithium aluminum hydride are introduced progressively and portionwise into 20 ml of dry tetrahydrofuran, under an atmosphere of nitrogen. The suspension obtained is cooled to 0° C., then a solution of 1.6 g of 3-chloro-6-methoxy-4-[2-(1-ethoxycarbonyl-4-piperidyl)-ethyl]-quinoline in tetrahydrofuran is added drop by drop. The reaction medium is maintained for 3 hours in an ice bath, then 0.45 ml of water, 0.33 ml of a 5 N aqueous solution of sodium hydroxide and 15 ml of water are added, very slowly and in the order given. The insoluble mineral products formed are separated by filtration and washed twice with 30 ml of methylene chloride. The filtrate and the washings are collected, dried over magnesium sulfate, then concentrated by evaporation. The residue obtained is fixed on a column of silica and eluted with a 90/10 mixture of chloroform and diethylamine. 0.9 g of 3-chloro-6-methoxy-4-[2-(1-methyl-4-piperidyl)-ethyl]-quinoline are thus obtained, the hydrochloride of which is amorphous.

N.M.R. spectrum of the product obtained:

| aromatics | δ: 7–8.7 ppm |
|---|---|
| CH$_2$N and CH$_2$Ar | δ: 2.4–3.4 ppm |
| CH$_3$O | δ: 3.9 ppm |

PHARMACOLOGICAL PROPERTIES

AFFINITY FOR THE CEREBRAL RECEPTOR SITES OF THE BENZODIAZEPINES

This affinity is measured by the capacity of the products for displacing the tritiated Diazepam ($^3$H Diazepam) from its binding site and is expressed by a value $K_i$, in micromoles (μM), which is calculated by the formula:

$$K_i = \frac{IC_{50}}{1 + \frac{C}{K_D}}$$

in which C represents the concentration of $^3$H Diazepam, $K_D$ is a constant of affinity equal to 2.74 μM and IC$_{50}$ is the concentration necessary to obtain an inhibition of 50% of the binding of the $^3$H Diazepam.

The products have been tested according to the method of Mohler et al., Life Science, 1977, 20, 2101, which is relied on herein. The following results have been obtained:

| Products | $K_i$ (μM) |
|---|---|
| Example 1 | 2 |
| 3 | 12 |
| 4 | 1 |
| 5 | 0.5 |
| 6 | 5 |
| 8 | 10 |
| 9 | 5 |

TOXICOLOGICAL PROPERTIES

The acute toxicities of the compounds according to the invention have been determined on the male mouse CD$_1$ (Charles RIVER) by the oral method. The LD$_{50}$ have been calculated, after 3 days observation, by the cumulative method of J. J. Reed and H. Muench (Amer. J. Hyg. 1938, 27, 493).

The compounds according to the invention behave like substances of relatively little toxicity towards mice, since the LD$_{50}$ of the compounds are between 200 and 1000 mg/kg.

THERAPEUTIC USE

The compounds of the invention and their pharmaceutically acceptable salts can be used in human therapeutics, in the form of compressed tablets, capsules, gelatin-coated pills, suppositories, ingestable or injectable solutions, etc., as hypnotics, anticonvulsants and for the treatment of states of anxiety and various psychoneurotic states.

The dosage depends on the effects desired and the method of administration used. For example, by oral administration, it can be between 5 and 250 mg of active substance per day, with single doses ranging from 1 to 50 mg.

Medicaments of the invention will contain as active principle a pharmaceutically active proportion of a compound of the invention and a pharmaceutically acceptable carrier.

What is claimed is:

1. Compounds of the general formula:

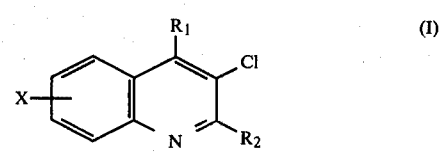

in which X is fixed in positions 5, 6, 7 or 8 of the quinoline ring and represents hydrogen, chlorine, or alkyl or alkoxy having 1 to 4 carbon atoms, one of the substituents R$_1$ and R$_2$ is hydrogen, alkyl having 1 to 4 carbon atoms or unsubstituted phenyl, and the other of the substituents R$_1$ and R$_2$ is a group of the formula:

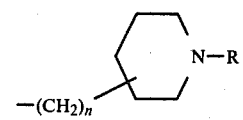

in which n is a whole number equal to 1 or 2, R is hydrogen or alkyl having 1 to 4 carbon atoms, and the radical (CH$_2$)$_n$ is fixed in position 3 or 4 on the piperidine ring, and their pharmaceutically acceptable salts of addition with mineral or organic acids.

2. Compounds according to claim 1 in which X is hydrogen, R₂ is hydrogen, methyl or phenyl, and R₁ is a group
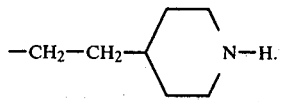
3. Compound according to claim 2 of the formula:
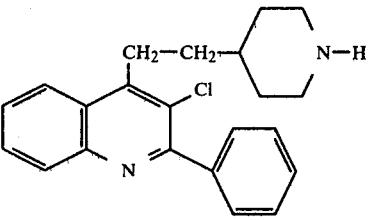
and its pharmaceutically acceptable salts of addition with mineral or organic acids.
4. Compounds according to claim 1 wherein R₂ is unsubstituted phenyl.
* * * * *